United States Patent [19]

Kirchhoff et al.

[11] Patent Number: 4,724,260

[45] Date of Patent: Feb. 9, 1988

[54] UNSATURATED ALKYL MONOARYLCYCLOBUTANE MONOMERS

[75] Inventors: Robert A. Kirchhoff; Alan K. Schrock; Stephen F. Hahn, all of Midland, Mich.

[73] Assignee: The Dow Chemical Company, Midland, Mich.

[21] Appl. No.: 835,013

[22] Filed: Feb. 28, 1986

Related U.S. Application Data

[63] Continuation-in-part of Ser. No. 644,849, Aug. 27, 1984, abandoned.

[51] Int. Cl.$^4$ ............................................ C07D 221/02
[52] U.S. Cl. .................................. 546/112; 556/489; 585/27; 526/258; 526/279; 526/281; 526/284
[58] Field of Search ............... 526/281, 284, 258, 279; 585/27; 556/489; 546/112

[56] References Cited

U.S. PATENT DOCUMENTS 4,540,763  9/1985  Kirchhoff ............................ 526/281
4,622,375  11/1986  Wong ................................... 526/284

OTHER PUBLICATIONS

Patterson, A. M., Capell, L. T. and Walker, D. F.; The Ring Index (Second Edition), American Chemical Society (1960): Ring Structure 833, p. 114.

*Primary Examiner*—Paul R. Michl
*Assistant Examiner*—Alex H. Walker
*Attorney, Agent, or Firm*—Stephen S. Grace

[57] ABSTRACT

Monomeric compositions comprising a monomer containing one arylcyclobutane moiety, and a molecular group comprising at least one unsaturated alkyl group are provided.

31 Claims, No Drawings

UNSATURATED ALKYL MONOARYLCYCLOBUTANE MONOMERS

CROSS-REFERENCE TO RELATED APPLICATION

This application is a continuation-in-part of copending U.S. application Ser. No. 644,849, filed on Aug. 27, 1984, now abandoned.

BACKGROUND OF THE INVENTION

This invention relates to monomers comprising a reactive arylcyclobutane moiety and an unsaturated alkyl moiety.

Thermoset resins are compositions which can solidify irreversibly upon heating. Such resins are useful in many engineering applications, such as for example, as coatings, structural laminates, adhesives, films, composites and the like. Examples of conventional forming techniques are transfer molding, compression molding, and hand lay-up processing.

Desirable thermoset resins possess chemical resistance, tensile strength, temperature resistance, electro-insulative or electro-conductive properties and other properties which encourage their use as engineering materials. Such properties depend on the chemical structure of the resin or materials added to the resin. For example, resins comprised of aromatic structures, especially aromatic polyamides and polyimides intrinsically possess thermal and oxidative stability. Unfortunately, the preparation and curing of such resins require the handling of highly toxic and volatile compositions. Furthermore, the resins are difficult to form in molding processes, and are at times undesirably insoluble in many organic solvents.

Another class of engineering polymeric compositions are thermoplastic polymeric compositions. Such compositions soften upon heating and can be formed into many useful shapes. Upon cooling, the compositions harden to the desired shapes. Advantageously, the polymeric compositions exhibit chemical resistance and are structurally durable. Examples of suitable thermoplastic polymeric compositions are those prepared from polycarbonate thermoplastic compositions.

In U.S. Pat. No. 4,540,763, poly(arylcyclobutane) polymers are disclosed. Such polymers are prepared from monomers which contain at least two arylcyclobutene moieties per monomer.

It would be desirable to have a new class of monomeric compositions, which are suitable for providing thermoset and/or thermoplastic engineering polymeric compositions.

SUMMARY OF THE INVENTION

This invention is a monomeric composition which comprises a monomer containing (a) one reactive arylcyclobutane moiety, and (b) a molecular group bonded to the aryl moiety. The molecular group contains at least one unsaturated alkyl group. Such monomers can be referred to as unsaturated alkyl monoarylcyclobutane monomers.

The monomeric compositions are useful for providing thermoset and/or thermoplastic engineering polymeric compositions. The monomeric compositions are useful in many engineering polymer applications such as, for example, in providing films for membranes, chemical and temperature resistant coatings for various solid substrates, composite materials and the like. In thermoset applications, the polymers can exhibit excellent physical properties and can be polymerized without the formation or use of volatile or toxic compositions.

DETAILED DESCRIPTION OF THE INVENTION

The monomeric compositions of this invention comprise an unsaturated alkyl monoarylcyclobutane monomer. Other compositions can be included in the monomeric composition such as copolymerizable monomers such as, for example, poly(arylcyclobutane) monomers or polymers, compositions miscible with the monoarylcyclobutane monomers which can be incorporated in the polymer matrix formed upon polymerization and the like. In polymerized form, the polymeric composition can be a homopolymer composition or an interpolymer composition.

The molecular group of this invention which is bonded to the aryl moiety is comprised of at least one unsaturated alkyl group, i.e., a group of two aliphatic or alicyclic carbon atoms bonded by a double or a triple bond. Examples of preferred molecular groups are aliphatic chains containing at least one pair of double-bonded or triple-bonded carbon atoms (i.e., alkenyl or alkynyl groups), heterocyclic groups containing at least one pair of double-bonded or triple-bonded carbon atoms, and the like.

The molecular group can also comprise an organic molecular group or an inorganic molecular group. Such additional molecular groups can bridge the aryl moiety with the unsaturated alkyl group, or the unsaturated alkyl group can bridge the aryl moiety with the additional molecular groups. Examples of suitable organic molecular groups are aliphatic, cycloaliphatic, heterocyclic and aromatic moieties. Such groups can contain oxygen, hydroxyl, amino-, amido-, sulfono-, halo-, transition metal, alkaline earth metal and other similar moieties. Suitable inorganic groups include, for example, oxygen, silicon, amino-, amido-, halo-, transition metal, alkaline earth metal moieties and the like.

The monomers of this invention comprise an arylcyclobutane moiety bonded to the unsaturated alkyl molecular group in a reactive position. The arylcyclobutane moiety is an aryl moiety which contains one or more cyclobutane rings fused to the aromatic ring. The arylcyclobutane moiety is in a reactive position when it is in a position such that under ring-opening conditions, addition polymerization sites are provided. Preferably, such a position is in a pendant position from the molecular group. Preferably, the molecular group is in a meta position from at least one of the cyclobutane carbon atoms. Aryl moieties are those referred to as aromatic compounds containing $(4N+2)\pi$ electrons as described in Morrison & Boyd, *Organic Chemistry*, 3rd ed., 1973. Suitable aromatic moieties include benzene, naphthalene, phenanthrene, anthracene, pyridine, a biaryl moiety or two or more aromatic moieties bridged by alkylene or cycloalkylene moieties. Preferred aromatic moieties are benzene, naphthalene, biphenyl, binaphthyl, diphenyl, alkene or diphenylcycloalkene moieties. The most preferred aromatic moiety is a benzene moiety. The aryl moiety can be substituted with a variety of electron-donating and electron-withdrawing moieties, which will further be defined.

Preferred unsaturated alkyl monoarylcyclobutene monomers of this invention wherein the unsaturated alkyl group is an alkenyl group can be represented by the formula

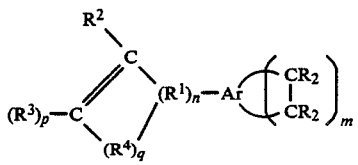   I wherein
- Ar is an aryl moiety;
- R, $R^2$ and $R^3$ are separately and independently in each occurrence hydrogen, an electron-donating moiety or an electron-withdrawing moiety;
- $R^1$ and $R^4$ are a polyvalent organic moiety or a polyvalent inorganic moiety;
- m is an integer of at least 1;
- n is an integer of 0 or 1;
- p is an integer of 1 or 2; and
- q is an integer of 0 or 1 provided that when n is 0, then the alkenyl group is directly bonded to the aryl moiety, q is 0, and p is 2; and when p is 2, then q is 0.

Separately and independently in each occurrence means that R, $R^2$ and $R^3$ can be different in each occurrence.

Preferred compounds corresponding to Formula I include compounds that when n is 0 or 1, q is 0 and p is 2, the molecular group can be a 1,2-alkenyl moiety, wherein $R^1$ is an alkyl group when n is 1. In another preferred compound, the molecular group can be a 1-aryl-alkenyl group, wherein n is 0 or 1, q is 0, p is 2 and at least one $R^3$ is an aromatic moiety. In yet another preferred compound, the molecular group contains a heteroatom, n is 1 and $R^1$ contains the heteroatom, q is 0 or 1 and p is 1 or 2. The molecular group can be a heterocyclic ring containing an ethylenically unsaturated group.

Preferred unsaturated alkyl monoarylcyclobutane monomers, wherein the unsaturated alkyl group is an alkynyl group can correspond to the formula

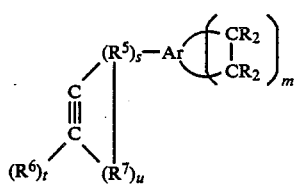   II wherein
- Ar, R, and m are defined as above;
- $R^6$ is a hydrogen, an electron-donating moiety, or an electron-withdrawing moiety;
- $R^5$ and $R^7$ are a polyvalent organic moiety, or a polyvalent inorganic moiety;
- s, is an integer of 0 or 1;
- t is an integer of 0 or 1; and
- u is an integer of 0 or 1; provided that when s is 0 then the alkynyl group is bonded directly to the aryl moiety, u is 0 and t is 1; when t is 1, then u is 0; and when u is 1, then s is 1, and t is 0.

Polyvalent inorganic moiety refers to any inorganic moiety which can bond to 2 or more other moieties. Such polyvalent inorganic moieties can be covalently or ionically bonded to the other moiety. Examples of polyvalent inorganic moieties include oxygen, phosphorus, phosphorus oxide, sulfur, nitrogen, silicon, polysiloxanes, polyvalent metals, sulfoxide, sulfone, a polyvalent metal bound to a polyvalent oxygenated moiety wherein the polyvalent oxygenated moiety can be further bound to an aryl moiety (for example, a polyvalent carboxylate salt). Preferred polyvalent inorganic moieties include oxygen, sulfur, silicon, polysiloxanes, and polyvalent metals bound to polyvalent oxygenated moieties.

The polyvalent organic moiety can be any polyvalent organic moiety bonded to 2 or more other moieties. The organic moiety can also contain one or more heteroatoms, comprising oxygen, nitrogen, phosphorus, or sulfur, or an organic moiety containing one or more aromatic moieties. Preferably, the polyvalent organic moiety is an alkyl poly-yl which is bonded to functionalized linking groups or an alkyl poly-yl which contains an aromatic moiety. Alkyl poly-yl is an alkyl moiety which is bonded to 2 or more linking groups, wherein the alkyl poly-yl can further contain one or more of the hereinbefore defined heteroatoms. Included within the term alkyl are any organic moieties containing carbon and hydrogen atoms. Suitable alkyl groups include the following organic moieties: alkanes, alkenes, alkynes, cycloalkanes, cycloalkenes, aromatic moieties wherein aromatic is as defined hereinbefore, alkyl-substituted aromatic moieties, and aryl-substituted aliphatic moieties.

Electron-donating moieties are molecular or nuclear groups which donate electrons more than a hydrogen atom would if accompanying the same site. Electron-withdrawing moieties are groups which more readily withdraw an electron relative to a hydrogen atom. Examples of suitable electron-withdrawing moieties include $-NO_2$, $-CN$, Br, I, Cl, F, $-PR_2$, $-CO_2H$, $-CO_2R$,

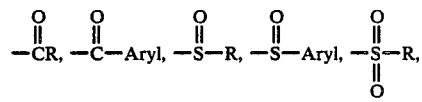

and aryl. Examples of suitable electron-donating groups include alkyl, aryl, alkoxy, aryloxy, hydrocarbyl, hydrocarbyloxy, hydrocarbylthio, $-OH$, $-OR$, $-NH_2$, $-NHR$, $-NR_2$. Hydrocarbyl refers to any organic moiety containing carbon and hydrogen atoms; hydrocarbyloxy refers to such organic moieties which further contain a hydroxyl moiety; and hydrocarbylthio refers to organic moieties which further contain a sulfur atom.

Preferably, the arylcyclobutane moiety is a benzocyclobutane moiety, wherein the aryl moiety, Ar, is a benzene moiety. The preferred alkenyl monoarylcyclobutanes can correspond to the formula

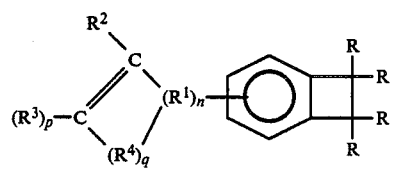   III wherein R, $R^1$, $R^2$, $R^3$, $R^4$, n, q and p are defined above, and m is 1.

The preferred alkynyl monoarylcyclobutane monomers correspond to the formula

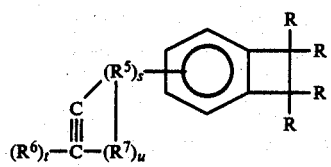

IV wherein R, $R^5$, $R^6$, $R^7$, s, t, and u are defined above; and m is 1. More preferably, u=0, and the alkenyl group is part of a molecular chain rather than a cyclic molecular group. The chain form is more stable.

A preferred ethylenically unsaturated monoarylcyclobutane monomer is an N-substituted arylcyclobutyl-unsaturated cyclic imide, which corresponds to the formula

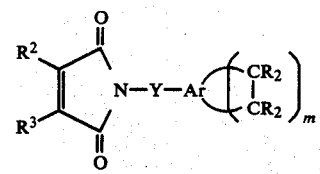

V wherein
Ar is an aromatic moiety;
R is separately in each occurrence hydrogen or an electron-withdrawing group;
$R^2$ and $R^3$ are separately in each occurrence hydrogen, a hydrocarbyl, hydrocarbyloxy or hydrocarbylthio group;
Y is a direct bond or a divalent organic moiety; and
m is an integer of at least 1.

Formula III corresponds to Formula I as follows: Ar, R, $R^2$ and $R^3$ are the same in both formulae; $R^1$ in Formula I is

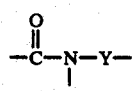

in Formula III; $R^4$ in Formula I is

in Formula III; n is 1, p is 1, and q is 1 in Formula III.

A more preferred embodiment is the N-substituted arylcyclobutenyl-unsaturated cyclic imide, which corresponds to the formula

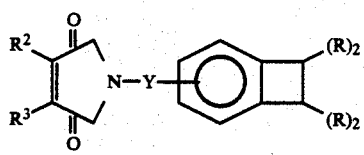

VI wherein
$R^2$ and $R^3$ are separately in each occurrence hydrogen, hydrocarbyl, hydrocarbyloxy or carbonitrile hydrocarbylthio; and
Y is a direct bond or a divalent organic moiety.

Preferred molecular groups are ethylenically unsaturated groups and aromatic moieties bridged by ethylenically unsaturated groups to the arylcyclobutane moiety. Preferably, the ethylenically unsaturated group is a vinyl group. When the arylcyclobutane is benzocyclobutane, the preferred monomers correspond to the formulae

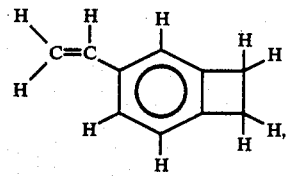

VII

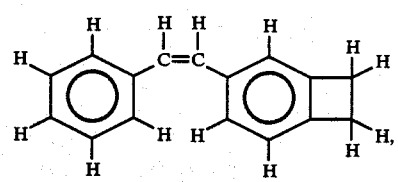

VIII

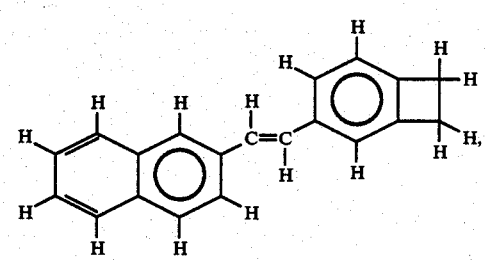

IX

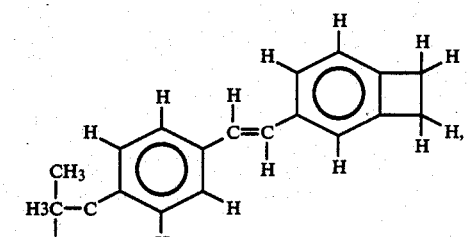

X

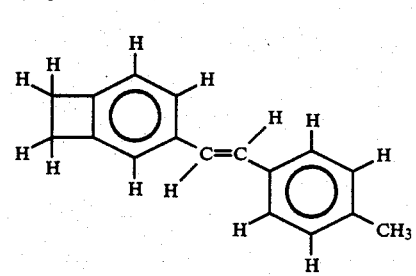

XI

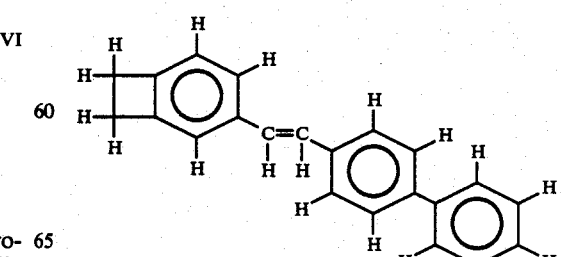

XII

-continued

XIII
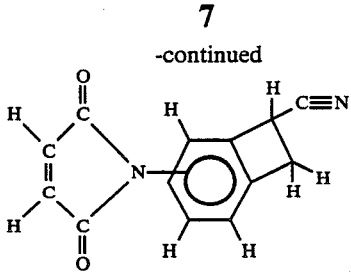

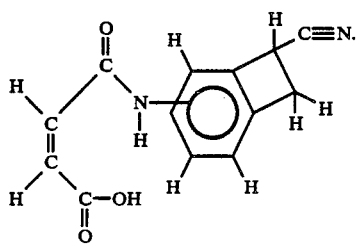

A more preferred alkynyl monoarylcyclobutane is 1-trimethylsily-2-(4-benzocyclobutyl)acetylene, and corresponds to the formula XV
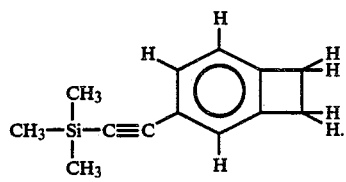

This formula corresponds to the general Formula IV as follows:

R in Formula IV is H in Formula XV; m in Formula IV is 1 in Formula XV; s in Formula IV is 0 in Formula XV and therefore $R^5$ in Formula IV is not present in Formula XV and the alkynyl group is bonded directly to the aryl moiety; u in Formula IV is 0 in Formula XV, and therefore $R^7$ is not present; t in Formula IV is 1, and $R^6$ in Formula IV is

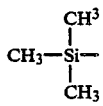

in Formula XV.

Another preferred alkynyl monoarylcyclobutane is 1-(4-benzocyclobutyl)-2-phenyl acetylene which corresponds to the formula XVI
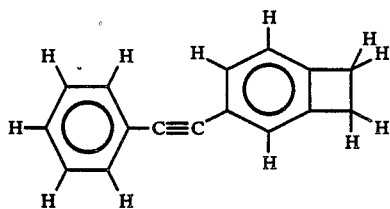

This formula corresponds to the general formula IV as follows:

R in Formula IV is H in Formula XVI; m in Formula IV is 1 in Formula XVI; s in Formula IV is 0 in Formula XVI and therefore $R^5$ in Formula IV is not present in Formula XVI and the alkynyl group is bonded directly to the aryl moiety; u in Formula IV is 0 in Formula XVI and therefore $R^7$ is not present in Formula XVI; t in Formula IV is 1, and $R^6$ in Formula IV is

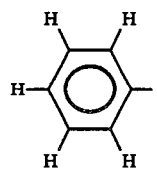

in Formula XVI.

The monomeric compositions of this invention can be prepared by reacting a suitably substituted arylcyclobutane compound with a molecular group containing ethylenic unsaturation, and a moiety reactive with the substituted arylcyclobutane. A variety of synthesis schemes are suitable, and examples are disclosed in U.S. Pat. No. 4,540,763 and U.S. Pat. No. 4,562,280, both herein incorporated by reference.

Typically, the unsaturated alkyl monoarylcyclobutane monomers of this invention can be prepared by reacting a brominated arylcyclobutane compound with a molecular compound containing an unsaturated alkyl group. An arylcyclobutane compound can be brominated by dissolving an arylcyclobutane in acetic acid and contacting a brominating agent of pyridinium perbromide hydrobromide in the presence of mercuric salts, for example, mercuric acetate, at a temperature of between about 20° C. and about 50° C. The brominated product can be recovered by extraction and distillation.

The brominated arylcyclobutane can be converted to an arylcyclobutane compound containing a different reactive substituent such as a carboxylic acid, ester, amine, amido, and the like. Such substituted arycyclobutane compounds can be reacted with molecular compounds containing correspondingly reactive substituents. An amine substituted arylcyclobutane can be reacted with a compound which contains at least one anhydride moiety to prepare an arylcyclobutane monomer containing a cyclic imide linking group. Also a carboxylate-substituted arylcyclobutane compound can be contacted with a compound containing an amine moiety to prepare an arylcyclobutane monomer containing an amido-linking group. Further, the bromo-substituted arylcyclobutane compound can be contacted with a compound containing a terminal unsaturated alkyl moiety (i.e., an alkenyl or alkynyl moiety) to prepare an arylcyclobutene monomer with an alkenyl or alkynyl molecular group substituted on the aryl moiety. Also, an ester substituted arylcyclobutane can be contacted with a primary aliphatic amine in a suitable diluent in the presence of heat to prepare an arylcyclobutane monomer with an amido aliphatic molecular group substituted on the aryl moiety.

A preferred compound, 4-vinylbenzocyclobutane (Formula VII), can be prepared by contacting an amount of 4-bromobenzocyclobutene with ethylene in a pressurized reactor in the presence of a palladium (II) acetate catalyst and a cocatalyst such as tri-o-tolylphosphine, and an appropriate base. After a suitable reaction temperature and time, 4-vinylbenzocyclobutane can be extracted in a suitable solvent.

To prepare the preferred monomer, 1-phenyl-2-(4-benzocyclobutyl)ethene (Formula VIII), an amount of 4-bromobenzocyclobutane is contacted with styrene in the presence of a palladium catalyst, a suitable diluent and a suitable base under a nitrogen atmosphere at reflux. The product can be recovered from an aqueous acid solution.

To prepare the preferred monomer, 1-naphthyl-2-(4-benzocyclobutyl)ethene (Formula IX), an amount of 4-bromobenzocyclobutane is contacted with an amount of vinylnaphthalene in the presence of a suitable catalyst at sufficient reaction temperatures.

To prepare the preferred monomer, 1-p-tert-butylphenyl-2-(4-benzocyclobutyl)ethene (Formula X), an amount of 4-bromobenzocyclobutane is contacted with an amount of para-tertiary butylstyrene in the presence of a suitable catalyst at sufficient reaction temperatures.

To prepare the preferred monomer of an arylcyclobutyl unsaturated cyclic imide (Formula XIII), a cyclic anhydride is contacted with an amine-substituted arylcyclobutane under conditions to form an arylcyclobutylamido alkylenoic acid. The acid can be dehydrated to cyclize the amidoalkylenoic acid into a cyclic imide ring and form the N-substituted arylcyclobutenyl unsaturated cyclic imide (Formula XIV).

To prepare the preferred monomer, 1-trimethylsily-2-(4-benzocyclobutyl)acetylene, (Formula XV) equal molar amounts of trimethylsilyl acetylene and 4-bromobenzocyclobutane are contacted in the presence of a suitable catalyst mixture. Suitable catalyst mixtures can comprise metal catalysts. Preferably, the catalyst mixture comprises catalytic amounts of bistriphenylphosphine palladium (II) chloride, triphenyl phosphine, and cuprous iodide. The arylcyclobutene and acetylene compounds are preferably added to the catalyst mixture in the presence of a suitable solvent. A preferred solvent is triethylamine. The reaction can be conducted at reflux for a suitable reaction time.

The preferred monomer 1-(4-benzocyclobutenyl)-2-phenyl acetylene (Formula XVI) can be prepared in a similar manner, with phenyl acetylene being substituted for the trimethylsilyl acetylene.

Unsaturated alkyl heterocyclic arylcyclobutane monomers can be prepared according to similar methods. For example, methods for preparing cyclobutapyridines and substituted cyclobutapyridines are disclosed by J. M. Riemann, and W. S. Trahanovsky in *Tetrahedron Letters*, No. 22, pp. 1867–1870, 1977 (cyclobuta[b]pyridine and cyclobuta[c]pyridine); and by W. D. Crow, A. N. Khan; and M. N. Paddoa-Row in *Australian Journal of Chemistry*, No. 28, pp. 1741–1754, 1975 (2-methylcyclobuta[b]pyridine). Methods suitable for preparing other substituted cyclobutapyridines are suggested in the following references for the indicated compounds: in *Organic Reactions*, Vol. I, p. 91 (2-aminocyclobuta[b]pyridine); in *Berichte*, No. 57, p. 791, and p. 1802, 1924 (2-hydroxycyclobuta[b]pyridine is prepared from 2-aminocyclobuta[b]pyridine); by Hatinger and Lieben in *Monatschaft*, No. 6, p. 279, 1885, and Rath, *Annalan Chemische*, No. 486, p. 71, 1931 (2-bromocyclobuta[b]pyridine is prepared from 2-hydroxycyclobuta[b]pyridine); and by Hatinger and Lieben, in *Monatschaft*, No. 6, p. 279, 1885 and by Rath in *Annalan Chemische*, No. 486, p. 71, 1931 (2-chlorocyclobuta[b]pyridine is prepared from 2-hydroxycyclobuta[b]pyridine).

The substituted heterocyclic arylcyclobutane compounds can be used to prepare alkenyl and alkynyl heterocyclic arylcyclobutane monomers. For example, a maleamic acid derivative of cyclobutapyridine can be prepared by contacting 2-aminocyclobutapyridine with maleic anhydride in the presence of a suitable organic solvent, such as chloroform at suitable reaction temperatures. To prepare a mono-cyclobutapyridine, about equal moles of 2-aminocyclobutapyridine and maleic anhydride are employed. The maleamic acid derivative of cyclobutapyridine can be employed to prepare 2-[N-maleimido]cyclobutapyridine by treating the maleamic acid derivative at suitable reaction temperatures in a suitable organic solvent, for example, sodium acetate in acetic acid. Suitable reaction temperatures include the range of 100° to 120° C.

In another example, 2-bromocyclobutapyridine can be employed to prepare 2-vinylcyclobutapyridines. The bromocyclobutapyridine is contacted with excess ethylene at suitable pressure in the presence of a suitable catalyst system and solvent, and at suitable reaction temperatures. Suitable catalyst systems include palladium (II) acetate; and a suitable cocatalyst is tri-o-tolylphosphine. Suitable solvents include acetonitrile, and suitable reaction temperatures include 125° C.

In yet another example, 2-bromocyclobutapyridine can be employed to prepare a monocyclobutapyridine monomer having a vinyl bridging member connecting the cyclobutapyridine moiety with an organic molecular group, such as an aromatic moiety. For example, to prepare 1-(4-methylphenyl)-2-((2-cyclobutapyridyl)ethene, an amount of 2-bromocyclobutapyridine is contacted with a substantially equal to slightly greater molar amount of 4-methylstyrene in the presence of a suitable catalyst system, in a suitable solvent under suitable reaction conditions. Suitable catalyst systems include palladium (II) acetate and a suitable cocatalyst includes tri-o-tolylphosphine. Suitable solvents include acetonitrile, and suitable reaction conditions include refluxing for a sufficient time.

Especially useful monomeric compositions are those comprised of monoarylcyclobutane monomers with a pendant unsaturated alkyl moiety, for example, 4-vinylbenzocyclobutane. Such compositions are useful because they contain separately active dual-polymerization sites. The pendant ethylenically unsaturated moiety can undergo conventional vinyl-polymerization reactions, and the cyclobutane ring can be opened and reacted later. The pendant arylcyclobutane group provides a means for providing latent polymerization ability to vinyl addition polymeric compositions. The pendant arylcyclobutane moiety can cause the formation of addition polymerization sites upon opening the cyclobutane ring. Such a mechanism is useful in crosslinking the polymeric composition and for grafting other monomers or polymers to the vinyl polymeric composition. Suitable grafting compositions are monomers and polymers which contain sites which undergo addition polymerization reactions under ring-opening conditions, such as other compositions containing reactive arylcyclobutane moieties, and compositions which exhibit dienophilic behavior.

The monomeric compositions of this invention are also useful in preparing polymeric compositions wherein the monomers are linked through the arylcyclobutane moieties. Other compositions which can undergo addition polymerization reactions under the ring-opening conditions can be included in the polymeric composition. Preferably, poly(arylcyclobutane) monomers are included. Examples of suitable moieties are other ethylenically unsaturated moieties, acetylenic moieties, and other arylcyclobutene moieties. The arylcyclobutene moiety can undergo simple addition polymerization reactions as well as Diels-Alder-type reactions.

For example, for benzocyclobutane monomers, the monomers undergoing simple addition polymerization can provide structures corresponding to the formulae:

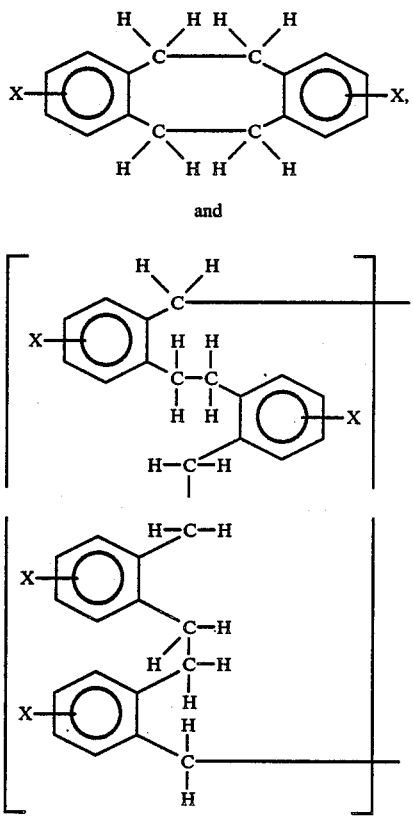

with the latter structure being more prevalent.

For the benzocyclobutane monomers undergoing Diels-Alder reactions, i.e., the cyclic imide benzocyclobutanes, compositions corresponding to the formula

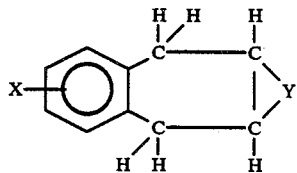

can be provided.

The monomeric compositions of this invention are useful in thermoset resin applications. The terminal cyclobutane ring opens under exposure to radiation, such as gamma-, electron-beam, and thermal radiation to provide addition polymerization sites. Preferably, thermal radiation is employed because it is applied via conventional methods, and can be applied in a variety of ways. Typically, temperatures from about 200° C. to about 300° C. are suitable to open the ring. Somewhat lower temperatures can open the ring when a metal catalyst is employed in the reaction. Suitable metal catalysts include copper salts. Once the ring is open, moieties which can undergo addition polymerization reactions can react at such sites. Typically, other opened cyclobutane rings will react thereto.

Depending upon the particular substituent on the arylcyclobutene moiety, the monoarylcyclobutene can be copolymerized with monomers useful in preparing thermoplastic polymeric compositions. Examples of such monomers are vinyl chloride, styrene, vinylidene chloride, and synthetic rubbers. For example, as mentioned above, vinylbenzocyclobutene can be copolymerized with styrene or other vinyl monomers.

In view of the fact that the monomeric compositions of this invention can readily polymerize under thermal radiation conditions, such compositions can be employed in compression molding and transfer molding processes, and as temperature activated adhesives. In compression molding, an amount of the monomeric composition is added to a mold with an effective amount of a suitable mold release agent. The mold is subjected to sufficient temperature and pressure conditions to provide a solid polymer or copolymer part.

In transfer molding, an amount of the monomeric composition is melted to a liquid, and then injected into a mold. The mold is at a temperature and under pressure sufficient to polymerize the monomer or comonomers and to provide a solid polymer or copolymer part.

As for adhesive, an amount of the monomeric composition can be coated onto a surface. Advantageously, the monomeric composition is first melted. The second surface to be adhered to the first is then contacted to the coated surface. The pieces can then be subjected to sufficient polymerization conditions to bond the two surfaces together.

Polymeric compositions prepared from the monomeric compositions of this invention exhibit excellent temperature and chemical resistance. They possess high glass transition temperatures, and water-insolubility. The polymers also possess high physical strength and durability. The polymeric compositions are highly useful in the electronics industry. Examples of such electronics uses include the preparation of passivation and planarization resins, die attach materials, composites and laminates for providing electronic circuit boards, encapsulation resins for integrated circuits, and the like.

A special use of the pendant unsaturated monoarylcyclobutane monomers, such as 4-vinylbenzocyclobutane, is as an inherent molecular fire retardant. As mentioned above, the pendant unsaturated monoarylcyclobutane monomer can be copolymerized with other vinyl polymerizable monomers such that the arylcyclobutene moiety provides latent polymerization sites. In view of the fact that such sites are thermally polymerizable, when exposed to sufficient heat, the cyclobutene rings will open and can crosslink with other opened rings. The crosslinked polymeric composition can thereby be a larger and more difficult composition to burn.

The following examples are illustrative only, and do not limit the scope of the invention.

EXAMPLE 1

Preparation of 1-Phenyl-2-(4-Benzocyclobutyl)ethene

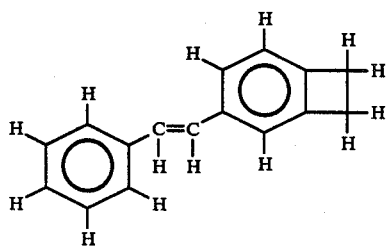

A solution of 2.4 g 4-bromobenzocyclobutane, 1.4 g styrene, 2.4 g tri-n-butylamine, 29 mg palladium (II) acetate, 100 mg of tri-o-tolylphosphine and 10 ml acetonitrile is stirred under nitrogen atmosphere at reflux for three hours. The reaction mixture is poured into 60 ml 10 percent HCl. The product is isolated by filtration, dried, recrystallized in ethanol, and isolated. About 2.10 g of greenish monomer product is prepared.

EXAMPLE 2

Preparation of 1-(2-Naphthyl)-2-(4-Benzocyclobutyl)ethene

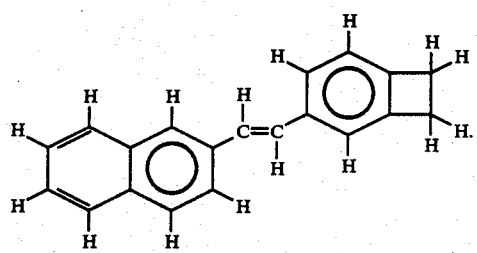

A solution of 3.0 g 4-bromobenzocyclobutane, 2.5 g 2-vinylnaphthalene, 3.0 g tri-n-butylamine, 150 mg tri-o-tolylphosphine, 36 mg palladium (II) acetate, and 10 ml acetonitrile is stirred at reflux under nitrogen atmosphere for 4 hours. The reaction mixture is poured into 60 ml of 10 percent HCl. The product is isolated by filtration, dried, recrystallized from ethanol, and isolated. About 1.8 g of monomer is prepared.

EXAMPLE 3

Preparation of 1-(p-tert-butylphenyl)-2-(4-benzocyclobutyl)ethene

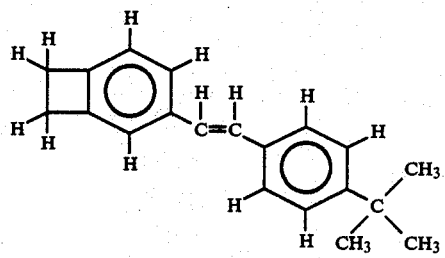

A solution of 3.0 g 4-bromobenzocyclobutane, 2.6 g 4-tert-butylstyrene, 3.0 g tri-n-butylamine, 150 mg tri-o-tolylphosphine, 36 mg palladium (II) acetate, and 10 ml acetonitrile is stirred under nitrogen at reflux for 4 hours. The reaction mixture is poured into 60 ml of 10 percent HCl. The product is isolated by filtration, dried, recrystallized from ethanol, and isolated. About 1.8 g of monomer is prepared.

EXAMPLE 4

Preparation of 4-Vinylbenzocyclobutane

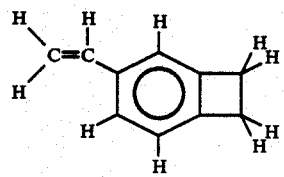

Into a 450 ml Parr pressure reactor, 100 ml of acetonitrile, and 0.6 g of freshly distilled triethylamine are added. The mixture is purged with nitrogen gas through a sparge tube for 15 minutes to remove air. To the reactor, 0.98 g of 4-bromobenzocyclobutane, 0.04 g of palladium (II) acetate, 0.17 g of tri-o-tolylphosphine are added and the reactor is sealed. The reactor is then pressurized with 250 psig ethylene, and is then vented. The reactor is pressurized with 2 more charges of 250 psig ethylene and is vented after each charge. The vessel is then pressurized to 250 psig ethylene, and held there. The mixture is then heated to 125° C. and is mechanically stirred for 16 hours. The reaction mixture is allowed to cool and the remaining ethylene is vented. The reaction mixture is worked up by washing in 100 ml diethyl ether, and this mixture is washed twice with 100 ml of water, once with 100 ml of 5 percent hydrochloric acid, once more with 100 ml of water, and is then dried over magnesium sulfate. The solvent is removed. The product is analyzed by gas chromatography, and it is determined that approximately 70 percent of the 4-bromopbenzocyclobutane is converted to 4-vinylbenzocyclobutene. The reaction mixture is passed through a 100 ml column of silica gel in the presence of hexane as an eluent. The hexane is removed on a rotary evaporator and the product is recovered.

EXAMPLE 5

Preparation of N-[5-(1-Cyanobenzocyclobutyl)]Maleamic Acid

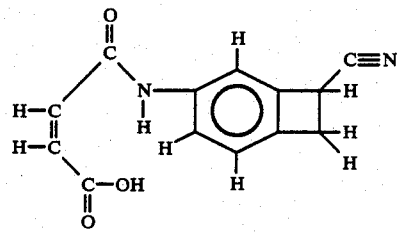

Into a 250 ml, 3-necked flask equipped with a mechanical stirrer, addition funnel, reflux condenser, thermometer and nitrogen inlet is placed 4.9 g (0.05 mole) of a freshly sublimed maleic anhydride and 50 ml of dried chloroform. The mixture is stirred under nitrogen while cooling to 15° C. in an ice bath and a solution of 7 g (0.05 moles) of 5-amino-1-cyanobenzocyclobutane and 50 ml of dried chloroform is added dropwise at such a rate as to keep the reaction mixture below 20° C. The reaction is maintained below 20° C. and stirred under nitrogen for one hour after addition is complete. The solid N-[5-(1-cyanobenzocyclobutenyl)]maleamic acid is filtered off, washed with chloroform and then with hot ethyl acetate/2-B ethanol (absolute: 1:1 v/v), and dried overnight in a vacuum at 60° C. The yield is 11.32 g equal to 94.25 percent and the melting point is between 190° C. and 192° C.

EXAMPLE 6

Preparation of N-[5-(1-Cyanobenzocyclobutyl)]Maleimide

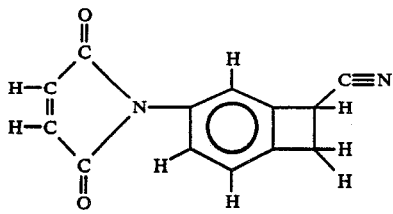

Into a 250 ml, 3-necked flask equipped with mechanical stirrer, reflux condenser, thermometer and nitrogen inlet is placed 11 g (0.045 moles) of N-[5-(1-cyanobenzocyclobutenyl)]maleamic acid, 2.4 g (0.03 moles) of anhydrous sodium acetate, and 45.94 g (0.765 mole) of fresh glacial acetic acid. The mixture is stirred and slowly heated under nitrogen until a clear yellow solution results (at about 117° C. and 118° C.). After 5 minutes, the heat is removed and the reaction mixture is allowed to cool under nitrogen overnight at room temperature. It is then slowly poured into a vigorously stirred slurry of ice and water (120 g total), and the resulting yellow precipitate filtered, washed with water until neutral to litmus, and transferred to a 500 ml beaker containing 150 ml of aqueous saturated sodium bicarbonate. This mixture is stirred for 10 minutes, then 150 ml of chloroform is added and stirred for an additional 10 minutes. The organic layer is taken up in three 50 ml portions of chloroform, and the solutions are combined and washed once with 150 ml of water. The chloroform solution is dried over anhydrous magnesium sulfate, filtered and evaporated on a rotary evaporator to give a viscous yellow oil. The product is pumped under vacuum overnight to give a yellow solid which is purified by column chromatography on silica gel using 70 percent toluene, 30 percent ethyl acetate as the eluent. The yield is 5.7 g equal to about 56.5 percent of theoretical. The melting point is between about 55° C. and 60° C.

EXAMPLE 7

Preparation of 1-(4-methylphenyl)-2-(4-benzocyclobutyl)ethene

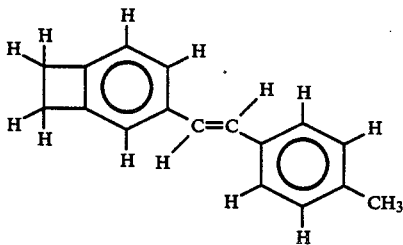

A solution of 3.0 g 4-bromobenzocyclobutane, 1.9 g 4-methylstyrene, 3.0 g tri-n-butylamine, 150 mg tri-o-tolylphosphine, 36 mg palladium (II) acetate, and 10 ml of acetonitrile is stirred at reflux under nitrogen for 4 hours. The reaction mixture is poured into 60 ml of 10 percent HCl. The product is isolated by filtration, dried, recrystallized from ethanol, and isolated. About 2.9 g of monomer is prepared.

EXAMPLE 8

Preparation of 1-(4-biphenyl)-2-(4-benzocyclobutyl)ethene

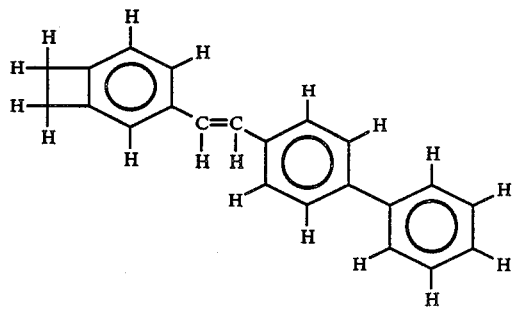

A solution of 3.0 g 4-bromobenzocyclobutane, 2.9 g 4-vinylbiphenyl, 3.0 g tri-n-butylamine, 150 mg tri-o-tolylphosphine, 36 mg palladium (II) acetate, and 10 ml of acetonitrile is stirred at reflux under nitrogen for 4 hours. The reaction mixture is poured into 60 ml of 10 percent HCl. The product is isolated by filtration, dried, recrystallized from ethyl acetate, and isolated. About 1.75 g of monomer is prepared.

EXAMPLE 9

Preparation of 1-trimethylsily-2-(4-benzocyclobutyl)acetylene

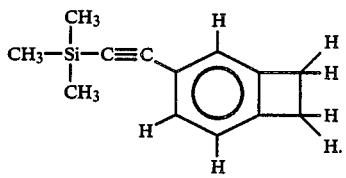

This reaction is run in a 100 ml 3-neck, round-bottom flask equipped with a reflux condenser topped with a gas inlet adapter and supplied with a positive nitrogen pressure via a mineral oil bubbler, a thermometer, magnetic stirrer, and a stopper. To this apparatus is added 0.013 g bistriphenylphosphine Palladium (II) chloride (M.W.=701.89 g, 0.07 mole percent), 0.055 g triphenyl phosphine (M.W.=262.3, 0.21 mmoles), and 0.014 g cuprous iodide (M.W.=190.44, 0.71 mmoles, 0.07 mole percent). To this catalyst mixture is added 35 ml triethylamine (distilled away from barium oxide), 5 g 4-bromobenzocyclobutane (M.W.=183, 27.3 mmoles), and 2.68 g trimethylsilyl acetylene (M.W.=98.22, 27.3 mmoles). This reaction mixture is refluxed using a heating mantle for 16 hours. After this time, the reaction mixture is allowed to cool, and a copious precipitate forms. This precipitate is removed via suction filtration to leave a yellow triethylamine solution. The solvent is removed via rotary evaporation, and gas chromatography of the resultant oil showed a mixture of starting material (ca. 15 percent) and product (ca. 85 percent). This mixture is then distilled under vacuum to give 2.75 g product better than 99 percent pure by G.C., boiling point 64° C. at ca. 1 torr, and the melting point is 35° to 37° C.

EXAMPLE 10

Preparation of 1-(4-Benzocyclobutyl)-2-Phenylacetylene

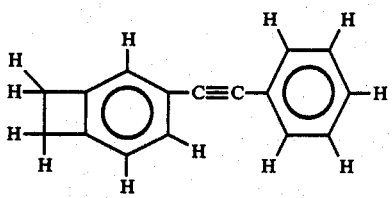

This reaction is run in a 100 ml 3-neck, round-bottom flask equipped with a reflux condenser topped with a gas inlet adapter and supplied with a positive nitrogen pressure via a mineral oil bubbler, a thermometer, magnetic stirrer, and a stopper. To this apparatus is added 0.013 g bistriphenylphosphine Palladium (II) chloride (M.W.=701.89 g, 0.07 mole percent), 0.055 g triphenyl phosphine (M.W.=262.3, 0.21 mmoles), and 0.014 g cuprous iodide (M.W.=190.44, 0.71 mmoles, 0.07 mole percent). To this catalyst mixture is added 35 ml triethylamine (distilled away from barium oxide), 5 g 4-bromobenzocyclobutane (M.W.=183, 27.3 mmoles), and 2.78 g phenylacetylene (M.W.=102, 27.3 mmoles). This reaction mixture is refluxed using a heating mantle for 16 hours. After this time, the reaction mixture is allowed to cool, and a copius precipitate forms. This precipitate is removed via suction filtration to leave a yellow triethylamine solution. The solvent is removed via rotary evaporation and the mixture is recrystallized from ethanol. The product is provided in about 75 percent yield and the product can be further purified by sublimation. The product has a melting point of between 51° and 53° C.

What is claimed is:

1. A monomeric composition comprising an unsaturated alkyl monoarylcyclobutane monomer containing (a) one reactive arylcyclobutane moiety, wherein the arylcyclobutane moiety is an aryl group which contains one or more cyclobutane rings fused to the aromatic ring, and (b) a molecular group bonded to the aryl group, wherein said molecular group contains at least one unsaturated alkyl group.

2. The composition of claim 1 wherein the unsaturated alkyl group is an alkenyl group.

3. The composition of claim 2, wherein the monomer corresponds to the formula

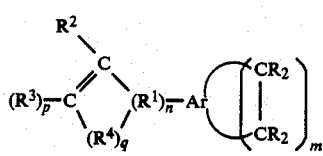

wherein

Ar is an aryl moiety;

R, $R^2$ and $R^3$ are separately and independently in each occurrence a hydrogen, an electron-donating moiety or an electron-withdrawing moiety;

$R^1$ and $R^4$ are a polyvalent organic moiety or a polyvalent inorganic moiety;

m is an integer of at least 1;

n is an integer of 0 or 1;

p is an integer of 1 or 2; and q is an integer of 0 or 1 provided that when n is 0 then the alkenyl group is directly bonded to the aryl group, q is 0, and p is 2; and when p is 2, then q is 0.

4. The composition of claim 3, wherein the molecular group is 1,2-alkenyl moiety wherein p is 2, q is 0, n is 0 or 1, and $R^1$ is an alkyl group when n is 1.

5. The composition of claim 3, wherein the molecular group is a 1-aryl-alkenyl group, wherein n is 0 or 1, q is 0, p is 2, and at least one $R^3$ is an aromatic moiety.

6. The composition of claim 3, wherein the molecular group contains an inorganic heteroatom; wherein n is 1 and $R^1$ contains the heteroatom; p is 1 or 2, and q is 0 or 1.

7. The composition of claim 3, wherein the aryl moiety, Ar, is a benzene moiety.

8. The composition of claim 4, wherein the aryl moiety, Ar, is a benzene moiety.

9. The composition of claim 5, wherein the aryl moiety, Ar, is a benzene moiety.

10. The composition of claim 6, wherein the aryl moiety, Ar, is a benzene moiety.

11. The composition of claim 8 wherein said monomer is 4-vinylbenzocyclobutane which corresponds to the formula

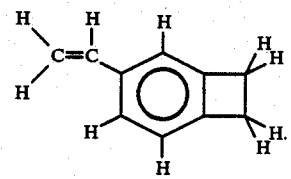

12. The composition of claim 9, wherein said monomer is 1-phenyl-(4-benzocyclobutyl)ethene, which corresponds to the formula:

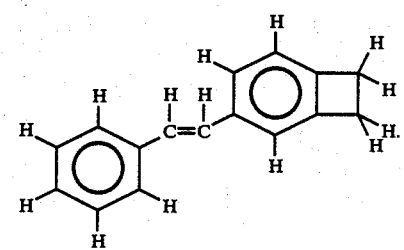

13. The composition of claim 9, wherein said monomeric composition comprises 1-naphthyl-2-(4-benzocyclobutyl)ethene which corresponds to the formula

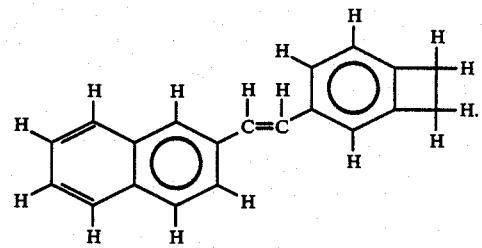

14. The composition of claim 9 wherein said monomer is 1-p-tertiarybutylphenyl-2-(4-benzocyclobutyl)ethene, which corresponds to the formula

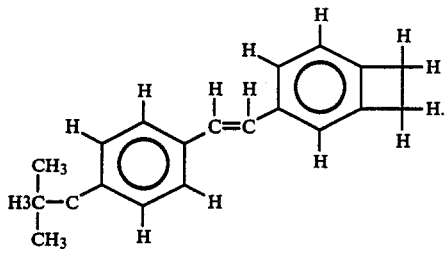

15. The composition of claim 11, wherein said monomeric composition further comprises an amount of a vinyl polymerizable monomer.

16. The composition of claim 15 wherein said vinyl polymerizable monomer is styrene.

17. The composition of claim 1 further comprising a poly(arylcyclobutane) monomer.

18. The composition of claim 3 further comprising a poly(arylcyclobutane) monomer.

19. The composition of claim 12 further comprising a poly(arylcyclobutane) monomer.

20. The composition of claim 13 further comprising a poly(arylcyclobutane) monomer.

21. The composition of claim 14 further comprising a poly(arylcyclobutane) monomer.

22. The composition of claim 1 wherein the unsaturated alkyl group is an alkynyl group.

23. The composition of claim 22, wherein the monomer corresponds to the formula

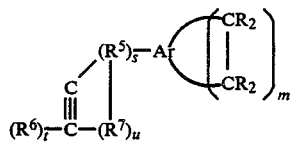

wherein
Ar is an aryl moiety,
R and $R^6$ are separately and independently in each occurrence hydrogen, an electron-donating moiety, or an electron-withdrawing moiety;
$R^5$ and $R^7$ are a polyvalent organic moiety, or a polyvalent inorganic moiety;
s is an integer of 0 or 1;
t is an integer of 0 or 1;
u is an integer of 0 or 1; and
provided that when s is 0 then the alkynyl group is bonded directly to the aryl moiety, u is 0 and t is 1; when t is 1, then u is 0; and when u is 1, then s is 1, and t is 0.

24. The composition of claim 23, wherein the monomeric composition comprises 1-trimethylsily-2-(4-benzocyclobutyl)acetylene which corresponds to the formula

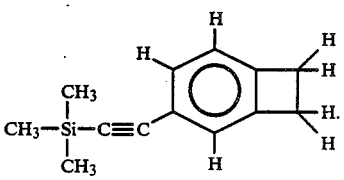

25. The composition of claim 24, further comprising a poly(arylcyclobutane) monomer.

26. The composition of claim 23, wherein the monomeric composition comprises 1-(4-benzocyclobutyl)-2-phenyl acetylene which corresponds to the formula

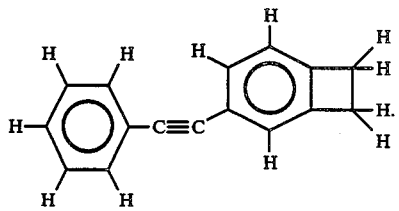

27. The composition of claim 26, further comprising a poly(arylcyclobutane) monomer.

28. The composition of claim 3, wherein the aryl moiety is a pyridine moiety.

29. The composition of claim 4, wherein the aryl moiety is a pyridine moiety.

30. The composition of claim 5, wherein the aryl moiety is a pyridine moiety.

31. The composition of claim 22, wherein the aryl moiety is a pyridine moiety.

* * * * *